United States Patent [19]
Hellemanns et al.

[11] 3,986,841
[45] Oct. 19, 1976

[54] APPARATUS FOR THE CONTINUOUS PRODUCTION OF SATURATED ALIPHATIC DICARBOXYLIC ACIDS

[75] Inventors: Gerhard Hellemanns; Hermann Röhl; Peter Hegenberg; Werner Eversmann, all of Marl, Germany

[73] Assignee: Chemische Werke Huls Aktiengesellschaft, Marl, Germany

[22] Filed: Jan. 29, 1975

[21] Appl. No.: 544,974

Related U.S. Application Data
[62] Division of Ser. No. 348,124, April 5, 1973, Pat. No. 3,880,921.

[30] Foreign Application Priority Data
Apr. 8, 1972  Germany............................ 2217003

[52] U.S. Cl. ............................... 23/288 A; 23/260; 23/263; 260/531 R
[51] Int. Cl.² ...................... C07C 51/18; B01J 8/08
[58] Field of Search ................. 23/288 R, 260, 263, 23/266, 285; 260/531 R, 537

[56] References Cited
UNITED STATES PATENTS

| | | | |
|---|---|---|---|
| 2,298,387 | 10/1942 | Kenyon et al. ............... | 260/531 R X |
| 2,557,282 | 6/1951 | Hamblet et al. ................ | 260/531 R |
| 2,761,768 | 9/1956 | Diels et al. ............................. | 23/266 |
| 3,053,881 | 9/1962 | Kremer et al. .................... | 23/260 X |
| 3,108,060 | 10/1963 | Matthews........................ | 23/260 X |
| 3,359,308 | 12/1967 | Sampson, Jr.................... | 260/537 X |
| 3,628,918 | 12/1971 | Beals et al. ....................... | 23/260 X |
| 3,673,245 | 6/1972 | Mims ............................. | 260/531 R |

*Primary Examiner*—James H. Tayman, Jr.
*Attorney, Agent, or Firm*—Millen, Raptes & White

[57] ABSTRACT

Apparatus for the continuous production of saturated aliphatic dicarboxylic acids by the catalyzed nitric acid oxidation of the corresponding cycloalkanols and cycloalkanones with recirculation of the reaction sludge and the reaction gases, which comprises cooling the reaction sludge by passing it through the tubes of a multiple tube heat exchanger, separating the reaction gases downstream of the heat exchanger, and dispersing the recycled portion of the reaction gases in the reaction sludge upstream of the heat exchanger, in a volume amount 0.1 to 2.0 times the volume of the reaction sludge circulating per unit time and in a pressure ratio of initial gas pressure to pressure in the circulation reactor at the gas feed point of $(x + 0.25) : x$ to $(x + 1.5) : x$, wherein $x$ is the pressure at the gas feed point, to form a homogeneously dispersed three-phase mixture of the recycled reaction gases in the reaction sludge in the tubes of the heat exchanger.

12 Claims, 1 Drawing Figure

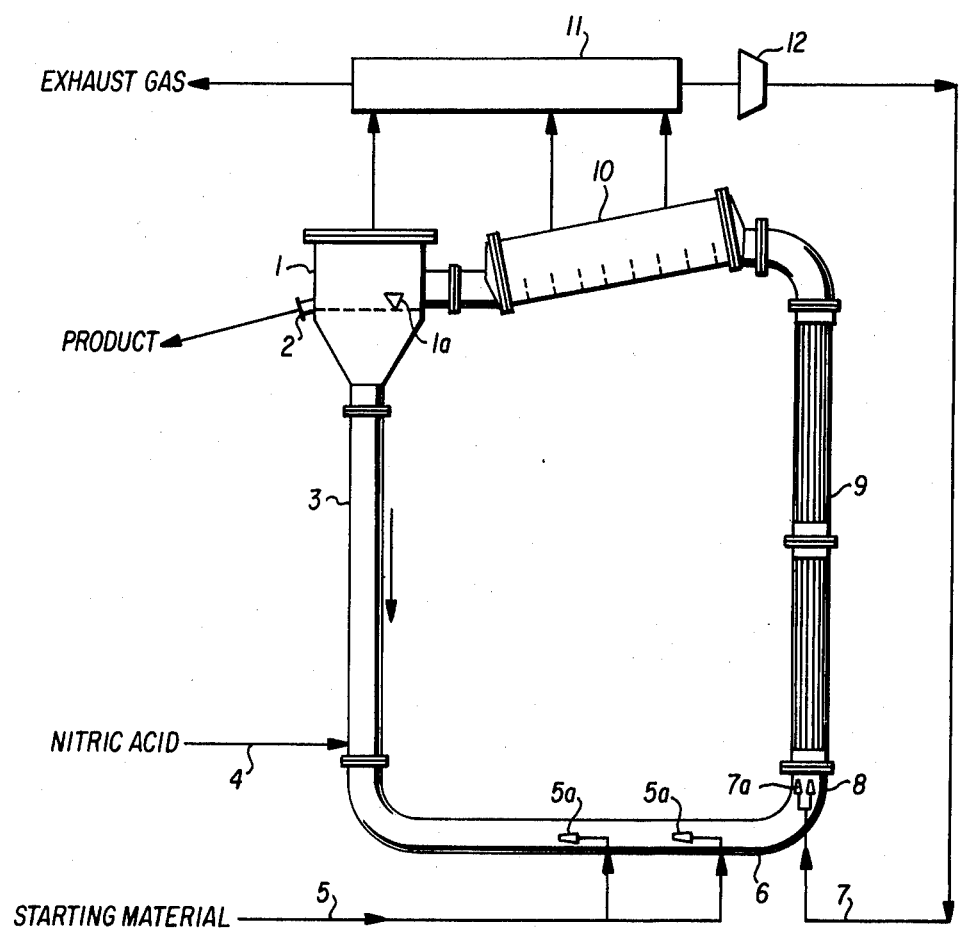

APPARATUS FOR THE CONTINUOUS PRODUCTION OF SATURATED ALIPHATIC DICARBOXYLIC ACIDS

This is a division of application Ser. No. 348,124 filed Apr. 5, 1973, now issued as U.S. Pat. No. 3,880,921 on Apr. 29, 1975.

BACKGROUND OF THE INVENTION

This invention relates to the continuous catalytic nitric acid oxidation of cycloalkanols and/or cycloalkanones to saturated aliphatic dicarboxylic acids, and to apparatus for conducting the process.

The oxidation of cycloalkanols and/or cycloalkanones with nitric acid to produce dicarboxylic acids is well known. See U.S. Pat. Nos. 2,439,513; 2,557,282; 2,831,024; 2,844,626; 2,878,276; 3,673,248; British Pat. No. 567,525; French Pat. No. 1,428,374. This process advantageously is conducted at low operating temperatures, such as about 20°–50° C. The prior-filed application of Rohl et al., Ser. No. 28,564, filed Apr. 15, 1970, claims such a process. The thus-produced dicarboxylic acid, in most cases, separates in the solid phase and tends to cling to the walls of the reactors in the form of an insulating crystalline layer. Theretofore, it has not been possible heretofore to successfully employ tube bundle heat exchange (tube-nest) reactors with external cooling, which are otherwise very effective in strongly exothermic reactions, unless the reaction is conducted in the homogeneous phase by the use of special measures, for example, very large dilution or the use of solubilizers.

German Pat. No. 844,144 mentions in passing the possibility of employing a vertically disposed tube bundle (tube-nest) surrounded by a cooling jacket as a reactor. However, no example is set forth in this connection and the specification does not give any further details.

German Published Application DAS No. 1,238,000, on the other hand, gives reasons why a tube-nest reactor should not be used, especially with respect to the process claimed in German Pat. No. 844,144. The utilization of a plurality of tubes of small cross section for the reaction results in difficulties in control technology, primarily because of the difficulty of feeding the reaction mixture through individual heat exchange tubes uniformly and cooling the contents of the various tubes to the same temperature. When there are different reaction conditions in the individual tubes, varying amounts of reaction gas are formed, so that the differences with respect to residence time and temperature characteristic in the individual tubes are magnified, resulting in a reduction in yield. Furthermore, due to deposition of the dicarboxylic acids on the walls, the narrow tubes of a tube-bundle heat-exchange reactor can easily be clogged, thus impairing the continuous operation of the process.

In U.S. Pat. Nos. 2,439,513 and 2,557,282, a reactor is described for use in a process for the preparation of adipic acid by nitric acid oxidation wherein the circulation vessel consists of a pipe cooled on all sides by a cooling jacket. Circulation in the reactor is provided by a pump. These patents also discuss the difficulty of product crystallizing on the cooled walls. Experiments conducted with a device as described in these United States patents and operated in accordance with the directions given in those patents, but using in place of a simple twin-jacket pipe an externally cooled tube nest, were not successful because the tubes continuously become clogged by the crystalline compound, due to insufficient circulation of the reaction sludge.

It is an object of this invention to eliminate the above-described disadvantages and to employ, in the above-described continuous oxidation with recycle of the reaction sludge and gases, a cooled tube-nest (tube bundle) heat exchanger, without the undesirable deposition of the thus-produced dicarboxylic acids on the tube walls, which makes maintenance of the reaction sludge at a uniform temperature impossible.

SUMMARY OF THE INVENTION

According to this invention, saturated aliphatic dicarboxylic acids are produced in a continuous process by the low temperature catalyzed nitric acid oxidation of the corresponding cycloalkanols, cycloalkanones and mixtures thereof with the reaction sludge being circulated through the tubes of a tube-nest circulation reactor, without clogging of the tubes or build-up of deposits on the walls thereof, by separating the nitrogen oxides formed during the oxidation and introducing them in finely dispersed form into the circulation reactor upstream from the tube bundle portion of the reactor relative to flow direction of the reaction mixture through the reactor, in a volume $0.1 - 2.0$ times per unit time the volume of reaction sludge circulating through the reactor and with a pressure ratio of the initial gas pressure of the recirculated gases at the point of insertion into the reaction sludge to the pressure in the circulation reactor at the gas feed point of $(x + 0.25):x$ to $(x + 1.5):x$, wherein $x$ is the pressure at the gas feed point.

DETAILED DISCUSSION

Suitable starting compounds are cyclic alkanols and alkanones and mixtures thereof, e.g., containing 6–16, preferably 6–12, especially 8–12, carbon atoms in the ring, such as, for example, cyclohexanol, cyclohexanone, trimethylcyclohexanol, tert.-butylcyclohexanol, and especially cyclododecanol, cyclododecanone, and mixtures thereof. From these starting materials, adipic acid, trimethyladipic acid, tert.-butyladipic acid and decanedicarboxylic acid-1,10, respectively, are obtained.

The nitric acid employed in the oxidation can vary fairly widely in strength. Usually 50–70% strength nitric acid is used, preferably in a 5- to 20-fold excess, based on the organic starting compounds. An 8- to 16-fold excess is particularly advantageous.

The oxidation can be conducted in the presence of any known catalyst for the reaction, e.g., a mercury, manganese, chromium or copper oxidation catalyst. For specific examples, see the prior art cited above. In general, a vanadium-containing catalyst is preferred, e.g., ammonium vanadate, sodium vanadate, or $V_2O_5$. The amount of such catalysts advantageously corresponds to approximately 0.01 to 0.1% by weight of vanadium, based on the nitric acid used, preferably 0.025 to 0.035% by weight. Higher amounts of catalyst are unnecessary. Moreover, they result in discolorations in the crude product and require additional purification steps during the working-up process. Co-catalysts, such as, for example, iron, chromium, and especially copper, which are frequently utilized in oxidations, are not necessary in the process of this invention and when using vanadium catalysts. The catalyst is added to the circulation reactor together with the nitric acid. Preferably, the catalyst is dissolved in the nitric acid prior to feeding the latter to the reactor.

The ambient temperature in the reaction sludge during the oxidation is of critical importance to the trouble-free conductance of the reaction and to the quality of the thus-produced dicarboxylic acid. Generally speaking, the lower the oxidation temperature, the higher the yield in dicarboxylic acid. Therefore, the process is carried out at a relatively low reaction temperature, i.e., usually about 20°–50° C., preferably about 30°–40° C.

The pressure in the circulation reactor can be between 1 and 10 atmospheres absolute, but is preferably 1.0 – 1.5 atm. abs. The pressure can be varied by throttling the gas discharge. Advantageously, lower pressures are employed because the operation can be conducted more economically.

Critical to achieving the advantages of the process of this invention is the introduction of the recycled reaction gases, i.e., the nitrogen oxides, upstream of the point of entrance of the reaction sludge into the multiple tube heat exchanger section of the circulation reactor. The recycled nitrogen oxides also must be fed into the circulating reaction in an amount and under a pressure such that a homogeneously dispersed three-phase mixture of the recycled nitrogen oxides in the reaction sludge, which contains suspended crystallized dicarboxylic acids, is produced. The pressure under which the nitrogen oxides are introduced through nozzles into the circulation reactor is dependent on the pressure ambient in the circulation reactor, the height of the liquid column in the circulation reactor, and the pressure loss during discharge into the stream of circulating reaction sludge. The height of the liquid column is determined by the technical design of the circulation reactor. The separated nitrogen oxides which are recycled are introduced into the circulation reactor in such a manner that the pressure ratio of the initial gas pressure at the point of introduction to the pressure in the circulation reactor at the gas feed point is $(x + 0.25) : x$ to $(x + 1.5) : x$, preferably $(x + 1) : x$, wherein $x$ is the pressure at the gas feed point. The gas is fed proximate the entrance of the reaction sludge into the part of the circulation reactor formed as a tube nest.

The circulated amount of nitrogen oxides must be large enough to produce a turbulent flow profile. This amount must be adapted to the total cross-sectional area of the tube nest, as well as to the cross-sectional area of the individual tubes of the tube nest, and also, in particular, to the volume of the reaction sludge circulated in unit time, and must be at least 0.1 times the volume of the volume of the reaction sludge circulated in unit time. The upper limit is about 2.0 times the volume of nitrogen oxides. Preferably, 0.2 to 1.5 times the volume of nitrogen oxides is employed, based on the volume of the reaction sludge circulated in unit time.

It has been found that, when introducing nitrogen oxides in an amount more than 0.5 times the volume of the reaction sludge circulated in unit time, the reaction sludge can be recirculated through the system exclusively or predominantly by the huge pump effect of the nitrogen oxides recycled under pressure into the system.

The recycled nitrogen oxides are introduced into the sludge in a manner such that the reaction sludge and recycled gases are homogeneously passed through the tubes of the heat exchanger. A nozzle is generally employed for this purpose.

In the process of this invention, no dicarboxylic acid crystallizes on the cooled walls of the tube nest at a reaction temperature of 20°–50° C. as a result of the turbulent and homogenous passage of the reaction sludge and recycled nitrogen oxides through the tubes, even with an average temperature difference between cooling water and reaction sludge of 1°–20° C., preferably 5°–15° C.

After removing the nitrogen oxides in a gas separator, a proportion of the circulating reaction sludge is withdrawn which corresponds to the introduced starting components, which proportion generally is about 0.5% of the total volume of circulating reaction sludge.

Thereafter, it is advantageous to degrade any nitrogen-containing organic compounds present in the withdrawn proportion of the sludge by a post-reaction heating at temperatures of between 70° and 90° C. At these temperatures the reaction mixture is a homogeneous phase. After cooling the crystalline dicarboxylic acid reaction product can then be separated from the reaction sludge in any convenient manner.

A suitable apparatus for conducting the continuous oxidation to saturated aliphatic dicarboxylic acids in accordance with the process of this invention is a closed loop circulation reactor, shown schematically in the drawing, with a receiver 1 containing a level sensor 1a and a product discharge conduit 2, a reaction sludge recycling unit 3, a nitric acid feed conduit 4, a starting material feed conduit 5, a mixing zone 6, nozzles 7 for introducing the nitrogen oxide into the circulating reaction sludge, a homogenizing zone 8, a multiple tube (tube-nest) heat exchanger with external cooling 9, a gas separator 10 and a nitrogen oxide recycling unit 11 with a compressor 12.

In the receiver 1, the crystalline reaction sludge from the gas separator 10 is collected after removal of the nitrogen oxides, and a portion thereof is withdrawn via conduit 2 for processing into saturated aliphatic dicarboxylic acids. The remaining reaction sludge flows via the reaction sludge recycling unit 3, where the consumed nitric acid is replenished by nitric acid feed conduit 4, and passes the starting product feed conduit 5 where the starting material, consisting of a cycloalkanol and/or cycloalkanone is admixed therewith. The mixing is ensured in mixing zone 6. Due to the feature of the nitrogen oxides being fed through the nozzles 7, the reaction sludge is converted into a three-phase mixture in which the gaseous phase is uniformly dispersed in the reaction sludge. This mixture, which has a highly turbulent flow characteristic, after passing through the homogenizing mixing zone 8, flows through the tube-nest (tube bundle) heat exchanger 9 as a homogenous turbulent mixture. In the tube nest heat exchanger 9 where the reactants are converted extensively to dicarboxylic acid, the heat of reaction is removed by indirect heat exchange. Thereafter, the reaction sludge flows into the gas separator 10, where the nitrogen oxides are separated and fed, via the nitrogen oxide recycling unit 11 with compressor 12, through recycle conduit 7 and nozzles 7a. The excess nitrogen oxides are fed, via a waste gas line, to a further processing stage. It is possible to additionally arrange a pump in the sludge cycle at any desired point, preferably in the reaction sludge recycling unit 3. This, however, will be unnecessary in most cases, since the amount of nitrogen oxides fed through the nitrogen oxide nozzles 7a is sufficient to effect circulation of the reaction sludge by the huge pump effect thereby achieved.

The nitric acid added to the system to compensate for the nitric acid loss incurred by the oxidation reaction is introduced into the circulation reaction at a distance upstream of the addition of the organic starting compounds into the zone of the reaction sludge recycling unit sufficient to ensure that the nitric acid is uniformly dispersed in the reaction sludge before contacting the organic starting materials. This distance generally should be 5 to 20 times the diameter of the backflow line in the region of the reaction sludge recycling section 3, in order to ensure uniform distribution. A special feeding device is not necessary.

In contrast thereto, the addition of the organic starting materials, namely the cycloalkanols and/or cycloalkanones should be carried out under intense intermixing by means of single- or multiple-jet nozzle elements 5a. Suitably, internally heated nozzle elements are employed. It is advantageous to introduce the starting compounds through the nozzles in opposition to the flow direction of the reaction sludge. For a better distribution of the starting compounds, it is advantageous to employ several nozzle elements. The starting materials are fed through feed conduit 5 to the circulation reactor between the feed point of the nitric acid and the feed point of the nitrogen oxides into the reactor.

It is essential that the thus-introduced organic starting compounds be dissolved in the circulating reaction sludge prior to entering the tube nest, and that adequate intermixing of the starting material in the reaction sludge occurs. Thus, a minimum residence time is required for the desired complete dissolution and intermixing of the organic starting compounds in the reaction sludge present in the circulation reactor before entering the heat exchanger portion of the circulating reactor, usually about 0.1 to 25 seconds, preferably 1 to 10 seconds. Only by the introduction of the nitrogen oxides into the circulation reactor is the catalyst activated in such a manner that the oxidation takes place at sufficient speed. Therefore, the distance of the nitrogen oxide feed point from the tube nest heat exchanger also is of importance. This distance is about 1 to 10 times the diameter of the pipeline in the feed zone of the circulation reactor, preferably 1.5 to 5.0 times this diameter. The nozzles for feeding the nitrogen oxides which can number from 1 to 30, preferably 10 to 20, are mounted upstream of and/or below the vertically disposed tube nest heat exchanger.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

In two mutually independent long-term experiments, the oxidation of cyclodecanol and a cyclodecanol/one mixture was conducted with an apparatus set up for continuous operation and corresponding to FIG. 1 under the conditions set forth in the Table below.

|  | Example 1 | Example 2 |
| --- | --- | --- |
| Organic starting material | Cyclododecanol | 80 % Cyclododecanol 20 % Cyclododecanone |
| Throughput Nitric Acid 63 % | 1.5 t./h. | 1.5 t./h. |
| Throughput Organic Starting Material | 0.15 t./h. | 0.15 t./h. |
| Ratio HNO$_3$:organic starting material | 10 : 1 | 10 : 1 |
| Sludge Circulation rate | 200 m$^3$/h. | 280 m$^3$/h. |
| Nitrogen oxides circulation rate | 100 Nm$^3$/h. | 130 Nm$^3$/h. |
| Circulating sludge to nitrogen oxides (at nozzles) ratio | 1 : 0.5 | 1 : 0.46 |
| Reactor Temp. Before tube reactor | 40° C. | 42° C. |
| Reactor Temp. After tube reactor | 39.3° C. | 41.5° C. |
| Fresh water rate | 5.7 t./h. | 7.3 t./h. |
| Cooling Water temp | 16° C. | 18° C. |
| Cooling Water rate | 40 t./h. | 20 t./h. |
| Cooling Water Temp. inlet tube reactor | 33° C | 28° C. |
| Cooling Water Temp. outlet tube reactor | 36° C. | 34° C. |
| Δ Inlet temp. cooling water to upstream reactor temp. | 7° C. | 14° C. |
| Distance between nitric acid feed point and starting material feed point to tube diameter (x times) | x = 8 | x = 8 |
| Distance between nitrogen oxide feed nozzles and tube reactor to tube diameter (x times) | x = 4 | x = 4 |
| Pressure: Nitrogen oxides (at nozzles) | 3.0 atm.abs. | 3.5 atm.abs. |
| Gas (downstream of separator) | 1.05 atm.abs. | 1.06 atm.abs. |
| Sludge Flow velocity (tube nest) | 2.1 m./sec. | 4.6 m./sec. |
| Residence time feed point organic starting material to tube reactor | 6 sec. | 4 sec. |
| Area cooling surface (tube reactor) | 28.3 m$^2$ | 16.0 m$^2$ | t = tons

When conducting the process of this invention, in the circulation reactor of this invention, with complete conversion, a yield of 96.5% of decanedicarboxylic acid (dodecanedioic acid) was obtained when using pure cyclododecanol, and a yield of 95.9% of decanedicarboxylic acid (dodecanedioic acid) was obtained when using a cyclododecanol/one mixture.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Apparatus for the continuous production of saturated aliphatic dicarboxylic acids by low temperature catalyzed nitric acid oxidation at about 20°–50° C. of a continuous stream of a corresponding cycloalkanol or cycloalkanone or a mixture thereof with a continuous stream of nitric acid comprising a circulation reactor having a receiver fitted with a product discharge conduit downstream from a gas discharge unit and mounted upstream of a reaction sludge recirculation unit, the sludge recirculation unit being fitted with a nitric acid feed inlet and a starting material feed inlet downstream of the nitric acid feed inlet, a first mixing zone downstream of the starting feed material inlet in which are fitted nozzles for injecting recycled nitrogen oxide reaction gases from the gas discharge unit into the reactor, a homogenizing mixing zone downstream from the first mixing zone, a multiple tube bundle heat exchanger with external cooling means downstream from the homogenizing mixing zone, a gas separator downstream from the heat exchanger and upstream from the receiver with product discharge conduit for separating the reaction gases from reaction sludge and a nitrogen oxide recycling unit between the gas separator and the first mixing zone fitted with a compressor for compressing a portion of the separated reaction gases and recycling them to said homogenizing zone.

2. An apparatus according to claim 1 wherein said feed inlet for the nitric acid is spaced from said starting compound feed inlet 5 to 20 times the diameter of the reflux line in the reaction sludge recirculation unit.

3. An apparatus according to claim 1 wherein said starting material inlet is positioned so as to provide a residence time for the starting material to the heat exchanger of 0.1 to 25 seconds.

4. An apparatus according to claim 3 wherein the residence time is 1 to 10 seconds.

5. An apparatus according to claim 3 wherein the outlet opening of said starting material feed inlet is oriented opposite the flow direction of the reaction sludge in the circulation reactor.

6. An apparatus according to claim 3 wherein the starting material is introduced in the reactor by a plurality of nozzle ements.

7. An apparatus according to claim 6 wherein the nozzle elements are internally heated.

8. An apparatus according to claim 1 wherein recycled reaction gases are introduced into the reactor through a plurality of nozzles spaced from the heat exchanger from 1 to 10 times the diameter of the reactor at the point where the reaction gases are introduced into the circulation reactor.

9. An apparatus according to claim 8 wherein the nozzles are spaced 1.5 to 5 times the diameter of the reactor at the point where the reaction gases are introduced into the circulation reactor.

10. An apparatus according to claim 1 wherein the recycled reaction gases are introduced into the circulation reactor through 10 to 20 nozzles positioned below a vertically disposed tube bundle heat exchanger.

11. An apparatus according to claim 1, wherein said feed inlet for the nitric acid is spaced from said starting compound feed inlet 5 to 20 times the diameter of the reflux line in the reaction sludge recirculation unit, said starting material inlet is positioned so as to provide a residence time for the starting material to the heat exchanger of 0.1 to 25 seconds, and recycled reaction gases are introduced into the reactor through a plurality of nozzles spaced from the heat exchanger from 1 to 10 times the diameter of the reactor at the point where the reaction gases are introduced into the circulation reactor.

12. An apparatus according to claim 1, wherein tubes of the multiple tube bundle heat exchanger are of constant diameter throughout the length thereof.

* * * * *